United States Patent [19]
Libermann et al.

[11] Patent Number: 5,721,113
[45] Date of Patent: Feb. 24, 1998

[54] NERF GENES

[75] Inventors: Towia Aron Libermann, Newton; Joerg Peter Oettgen, Brookline, both of Mass.; Charles A. Kunsch, Germantown, Md.

[73] Assignee: Human Genome Sciences, Inc., Rockville, Md.

[21] Appl. No.: 368,281

[22] Filed: Jan. 3, 1995

[51] Int. Cl.$^6$ ............... C12N 15/12; C12N 15/63; C12N 5/10; C07H 21/00

[52] U.S. Cl. ............... 435/69.1; 435/320.1; 435/252.3; 435/325; 536/23.5; 536/24.31

[58] Field of Search ............... 536/23.5, 24.31; 435/69.1, 240.1, 240.2, 252.3, 320.1; 935/70, 72, 9

[56] References Cited

PUBLICATIONS

Shimizu, K. et al., "An ets–related gene, ERG, is rearranged in human myeloid leukemia with t(16;21) chromosomal translocation", *Proc. Natl. Acad. Sci. USA*, 90, pp. 10280–10284 (1993).

Lopez, M. et al., "ERP, a New Member of the ets Transcription Facotr/Oncoprotein Family: Cloning, Characterization, and Differential Expression during B–Lymphocyte Development", *Molecular and Cellular Biology*, 14, No. 5, pp. 3292–3309, (1994).

Prasad, D.D.K. et al., "Structure and Expression of Human Fli–1 Gene", *Cancer Research*, 52, pp. 5833–5837 (1992).

Golub et al., "Fusion of PDGF Receptor β to a Novel ets–like Gene, tel, in Chronic Myelomonocytic Leukemia with t(5; 12) Chromosomal Translocation", *Cell* 77, pp. 307–316 (1994).

Leiden et al. J. Virology 66 (1992) 5890–5897.
Leiden et al.—Genbank Data Base p. 5—Nerf–1.
Leiden et al.—"Genbank Data Base" p. 5—Nerf–2.

*Primary Examiner*—Paula K. Hutzell
*Assistant Examiner*—Robert C. Hayes
*Attorney, Agent, or Firm*—Kirk Baumeister; Edward T. Lentz

[57] ABSTRACT

Isolated nucleic acids encoding human lymphoid-specific transcription factors NERF-1 and NERF-2, proteins obtainable from the nucleic acids, recombinant host cells transformed with the nucleic acids and use of the proteins and nucleic acid sequences are dislcosed.

10 Claims, No Drawings

NERF GENES

FIELD OF THE INVENTION

The present invention relates to isolated NERF-1 and NERF-2 genes; to essentially pure NERF-1 and NERF-2 proteins; and to compositions and methods of producing and using NERF-1 and NERF-2 DNA sequences and proteins.

BACKGROUND OF THE INVENTION

The ets gene family traces its history to oncogenes originally cloned from retroviruses. Since then, a number of cellular homologues have been cloned. It is now known that the ets gene family encodes a group of proteins which function as transcription factors under physiological conditions and transform cells when aberrantly expressed. Ets-related factors have been implicated in the transcriptional regulation of various genes in different cell types. In particular, in B- and T-lymphocytes as well as in macrophages, several members of this family are crucial for the cell- and differentiation-specific expression of certain genes. Members of the family include ERP, SAP-1, ELK-i, YAN, ERG, FLI-1, D-ELG, GABP-α, E4TF1-60, ER71, ETS-1, ETS-2, C-ETS-2, D-ETS-2, ETS-3, ETS-4, ETS-6, E74, ELF-1, ER81, PEA3, tel, Spi-1/Pu.1 and Spi-B.

Different stages of embryonic pluripotent cell development into specific cell types at programmed time points are characterized by differential expression of specific gene sets, and in the case of B- and T-lymphocytes, by differential gene rearrangement as well. Differential expression and/or activation of transcription factors leading to stage-specific expression of a certain set of genes appear to be crucial for cell diffentiation in general and B- and T-lymphocyte development in particular. Transcription factors from the ets gene family play a role in these processes of B- and T-lymphocyte-specific gene expression.

It has been observed that many of the oncogenes and tumor suppressor genes encode transcription factors and that the ets gene family products can, if abberantly expressed, cause cellular transformation. At least three ets-related genes, Fli-1 (Prasad et al., *Cancer Res.* 52, 5833–5837 (1992)), ERG (Shimizu et al., *Proc. Natl. Acad. Sci. USA* 90, 10280–10284 (1993)) and tel (Golub et al., *Cell* 77, 307–316 (1994)) have been directly implicated in human tumor formation.

Additionally, chromosomal translocations involving transcription factor genes appear to be especially frequent in human leukemias and lymphomas. For example, human chromosome 12 is involved in translocations in acute myeloid and lymphoblastic leukemia and in several other neoplasms. Two ets-related genes, ERP and tel, have been mapped to human chromosome 12 (Lopez et al., *Mol. Cell. Biol.* 14, 3292–3309 (1994), Golub et al., supra), and tel has been shown to be involved in at least some of these translocations (Golub et al., supra).

Members of the ets family have recently been shown to play essential roles as transcriptional regulators of a whole set of genes including many B- and T-cell-specific genes such as interleukin-2, CD3, CD4, T-cell receptors, lck, immunoglobulin heavy and light chain, TdT, mb-1, B29 and human immunodeficiency virus type 2 (HIV-2) long terminal repeat (LTR), stromelysin, jun-B, c-fos and urokinase. For example, the ets family member ELF-1 has been shown to regulate transcription of the viruses HIV-2, HTLV-1, the T-cell cytokines IL-2, IL-3 and GM-CSF and the T-cell genes CD4 and lck. ELF-1 has also been shown to interact with the retinoblastoma gene product which is involved in the cell cycle and acts as a tumor suppressor gene.

Most, if not all, ets-related factors interact with specific transcription factors of other transcription factor families. Further, the majority of ets-related factors are involved in growth regulation and differentiation of cells and are regulated by all of the major signal transduction pathways.

The involvement of members of the ets gene family in human cancer development, regulation of transcription in retrovirus replication and T-cell cytokine production, cell cycle effects, growth regulation, cellular differentiation and interaction with other transcription factors necessitates the identification of other novel members of this family. A need also exists for compounds which modulate the activity of novel ets family members, for methods to identify modulators of their activity and for reagents useful in such methods.

SUMMARY OF THE INVENTION

Accordingly, one aspect of the present invention is an isolated polynucleotide selected from the group consisting of:

(a) a polynucleotide encoding NERF-1 having the nucleotide sequence as set forth in SEQ ID NO:1 from nucleotide 122 to 1684;

(b) a polynucleotide capable of hybridizing to the complement of a polynucleotide according to (a) under moderately stringent hybridization conditions and which encodes a functional NERF-1; and (c) a degenerate polynucleotide according to (a) or (b).

Another aspect of the invention is an isolated polynucleotide selected from the group consisting of:

(a) a polynucleotide encoding NERF-2 having the nucleotide sequence as set forth in SEQ ID NO:3 from nucleotide 207 to 1949;

(b) a polynucleotide capable of hybridizing to the complement of a polynucleotide according to (a) under moderately stringent hybridization conditions and which encodes a biologically active NERF-2; and (c) a degenerate polynucleotide according to (a) or (b).

Another aspect of the invention is a functional polypeptide encoded by the polynucleotides of the invention.

Another aspect of the invention is a method for preparing essentially pure NERF-1 or NERF-2 protein comprising culturing a recombinant host cell comprising a vector comprising a polynucleotide of the invention under conditions promoting expression of the protein and recovery thereof.

Another aspect of the invention is an antisense oligonucleotide comprising a sequence which is capable of binding to the polynucleotides of the invention.

Another aspect of the invention is a modulator of the polypeptides of the invention.

Another aspect of the invention is a method for assaying a medium for the presence of a substance that modulates NERF activity comprising the steps of:

(a) providing a NERF protein having the amino acid sequence of NERF-1 (SEQ ID NO:2) or NERF-2 (SEQ ID NO:4) or a functional derivative thereof and a cellular binding partner;

(b) incubating with a test substance which is suspected of modulating NERF activity under conditions which permit the formation of a NERF gene product/cellular binding partner complex;

(c) assaying for the presence of the complex, free NERF protein or free cellular binding partner; and (d) comparing to a control to determine the effect of the substance.

Another aspect of the invention is NERF protein modulating compounds identified by the assay method of the invention.

Another aspect of the invention is a method for the treatment of a patient having need to modulate NERF-1 or NERF-2 activity comprising administering to the patient a therapeutically effective amount of the NERF protein modulating compounds of the invention.

Another aspect of the invention is a method for the treatment of a patient having need of NERF-1 or NERF-2 comprising administering to the patient a therapeutically effective amount of a polypeptide of the invention.

Yet another aspect of the invention is a pharmaceutical composition comprising a polypeptide of the invention and a pharmaceutically acceptable carrier.

DETAILED DESCRIPTION OF THE INVENTION

As used herein, the term NERF genes refers to DNA molecules comprising a nucleotide sequence that encodes the new ets-related factor 1 (NERF-1) and new ets-related factor 2 (NERF-2) transcription factors. The human NERF-1 gene sequence is listed in SEQ ID NO:1. The coding region of the NERF-1 gene consists of nucleotides 122–1684 of SEQ ID NO:1. The deduced 521 amino acid sequence of the NERF-1 gene product is listed in SEQ ID NO:2. The human NERF-2 gene sequence is listed in SEQ ID NO:3. The coding region of the NERF-2 gene consists of nucleotides 207–1949 of SEQ ID NO:3. The deduced 581 amino acid sequence of the NERF-2 gene product is listed in SEQ ID NO:4.

As used herein, the term "functional fragments" when used to modify a specific gene or gene product means a less than full length portion of the gene or gene product which retains substantially all of the biological function associated with the full length gene or gene product to which it relates. To determine whether a fragment of a particular gene or gene product is a functional fragment one merely generates the fragments by well-known nucleolytic or proteotytic techniques and tests the generated fragments for the described biological function.

As used herein, an "antigen" refers to a molecule containing one or more epitopes that will stimulate a host's immune system to make a humoral and/or cellular antigen-specific response. The term is also used herein interchangeably with "immunogen."

As used herein, the term "epitope" refers to the site on an antigen or hapten to which a specific antibody molecule binds. The term is also used herein interchangeably with "antigenic determinant" or "antigenic determinant site."

As used herein, "monoclonal antibody" is understood to include antibodies derived from one species (e.g., murine, rabbit, goat, rat, human, etc.) as well as antibodies derived from two (or perhaps more) species (e.g., chimeric and humanized antibodies).

As used herein, a coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

As used herein, a "replicon" is any genetic element (e.g., plasmid, chromosome, virus) that functions as an autonomous unit of DNA replication in vivo; i.e., capable of replication under its own control.

As used herein, a "vector" is a replicon, such as a plasmid, phage, or cosmid, to which another DNA segment may be attached so as to bring about the replication of the attached segment.

As used herein, a "reference" gene refers to the NERF-1 and NERF-2 gene sequence of the invention and is understood to include the various sequence polymorphisms that exist, wherein nucleotide substitutions in the gene sequence exist, but do not affect the essential function of the gene product.

As used herein, a "mutant" gene refers to NERF-1 and NERF-2 gene sequences different from the reference gene wherein nucleotide substitutions and/or deletions and/or insertions result in impairment of the essential function of the gene product.

As used herein, a DNA "coding sequence of" or a "nucleotide sequence encoding" a particular protein, is a DNA sequence which is transcribed and translated into a polypeptide when placed under the control of appropriate regulatory sequences.

As used herein, a "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein, DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

As used herein, a control sequence "directs the expression" of a coding sequence in a cell when RNA polymerase will bind the promoter sequence and transcribe the coding sequence into mRNA, which is then translated into the polypeptide encoded by the coding sequence.

As used herein, a "host cell" is a cell which has been transformed or transfected, or is capable of transformation or transfection by an exogenous DNA sequence.

As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

As used herein, "transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.), or by infection, in which viruses are used to transfer DNA into cells.

As used herein, a "target cell" is a cell(s) that is selectively transfected over other cell types (or cell lines).

As used herein, a "clone" is a population of cells derived from a single cell or common ancestor by mitosis. A "cell line" is a clone of a primary cell that is capable of stable growth in vitro for many generations.

As used herein, a "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, a "modulator" of a polypeptide is a substance which can affect the polypeptide function.

As used herein, a "replication-deficient virus" is a virus in which the excision and/or replication functions have been altered such that after transfection into a host cell, the virus is not able to reproduce and/or infect addition cells.

An aspect of the present invention is isolated polynucleotides encoding a NERF-1 or NERF-2 protein and substantially similar sequences. Isolated polynucleotide sequences are substantially similar if they are capable of hybridizing under moderately stringent conditions to SEQ ID NO:1 or SEQ ID NO:3 or they encode DNA sequences which are degenerate to SEQ ID NO:1 or SEQ ID NO:3 or are degenerate to those sequences capable of hybridizing under moderately stringent conditions to SEQ ID NO:1 or SEQ ID NO:3.

Moderately stringent conditions is a term understood by the skilled artisan and has been described in, for example, Sambrook et al. *Molecular Cloning: A Laboratory Manual,* 2nd edition, Vol. 1, pp. 101–104, Cold Spring Harbor Laboratory Press (1989). An exemplary hybridization protocol using moderately stringent conditions is as follows. Nitrocellulose filters are prehybridized at 65° C. in a solution containing 6X SSPE, 5X Denhardt's solution (10 g Ficoll, 10 g BSA and 10 g polyvinylpyrrolidone per liter solution), 0.05% SDS and 100 ug/ml tRNA. Hybridization probes are labeled, preferably radiolabelled (e.g., using the Bios TAG-IT® kit). Hybridization is then carried out for approximately 18 hours at 65° C. The filters are then washed twice in a solution of 2X SSC and 0.5% SDS at room temperature for 15 minutes. Subsequently, the filters are washed at 58° C., air-dried and exposed to X-ray film overnight at −70° C. with an intensifying screen.

Degenerate DNA sequences encode the same amino acid sequence as SEQ ID NO:2 and SEQ ID NO:4 or the proteins encoded by those sequences capable of hybridizing under moderately stringent conditions to SEQ ID NO:1 or SEQ ID NO:3, but have variation(s) in the nucleotide coding sequences.

Alternatively, substantially similar sequences are defined as those sequences in which about 66%, preferably about 75% and most preferably about 90%, of the nucleotides or amino acids match over a defined length of the molecule. As used herein, substantially similar refers to the sequences having similar identity to the sequences of the instant invention. Thus nucleotide sequences that are substantially the same can be identified by hybridization or by sequence comparison. Protein sequences that are substantially the same can be identified by techniques such as proteolytic digestion, gel electrophoresis and/or microsequencing. Excluded from the definition of substantially similar sequences are the ets gene family members ERP, SAP-1, ELK-1, YAN, ERG, FLI-1, D-ELG, GABP-, E4TF1-60, ER71, ETS-1, ETS-2, C-ETS-2, D-ETS-2, ETS-3, ETS-4, ETS-6, E74, ELF-1, ER81, PEA3, tel, Spi-1/Pu.1 and Spi-B.

Embodiments of the isolated polynucleotides of the invention include DNA, genomic DNA and RNA, preferably of human origin. A method for isolating a nucleic acid molecule encoding a NERF protein is to probe a genomic or cDNA library with a natural or artificially designed probe using art recognized procedures. See, e.g., "Current Protocols in Molecular Biology", Ausubel et al. (eds.) Greene Publishing Association and John Wiley Interscience, New York, 1989,1992. The ordinarily skilled artisan will appreciate that SEQ ID NO:1, SEQ ID NO:3 or fragments thereof comprising at least 15 contiguous nucleotides are particularly useful probes. It is also appreciated that such probes can be and are preferably labeled with an analytically detectable reagent to facilitate identification of the probe. Useful reagents include, but are not limited to, radioisotopes, fluorescent dyes or enzymes capable of catalyzing the formation of a detectable product. The probes would enable the ordinarily skilled artisan are to isolate complementary copies of genomic DNA, cDNA or RNA polynucleotides encoding NERF proteins from human, mammalian or other animal sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another aspect of the invention is functional polypeptides encoded by the polynucleotides of the invention. An embodiment of a functional polypeptide of the invention is the NERF-1 protein having the amino acid sequence set forth in SEQ ID NO:2. Another embodiment is the NERF-2 protein having the amino acid sequence set forth in SEQ ID NO:4.

Another aspect of the invention is a method for preparing essentially pure NERF-1 or NERF-2 protein. Yet another aspect is the NERF-1 and NERF-2 proteins produced by the preparation method of the invention. These proteins have the amino acid sequences listed in SEQ ID NO:2 and SEQ ID NO:4, respectively, and include variants with a substantially similar amino acid sequence that have the same function. The proteins of this invention are preferably made by recombinant genetic engineering techniques by culturing a recombinant host cell containing a vector encoding the polynucleotides of the invention under conditions promoting the expression of the protein and recovery thereof.

The isolated polynucleotides, particularly the DNAs, can be introduced into expression vectors by operatively linking the DNA to the necessary expression control regions, e.g., regulatory regions, required for gene expression. The vectors can be introduced into an appropriate host cell such as a prokaryotic, e.g., bacterial, or eukaryotic, e.g., yeast or mammalian cell by methods well known in the art. See Ausubel et al., supra. The coding sequences for the desired proteins, having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include, but are not limited to, the bacteriophage (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, a Drosophila insect system, YCp19 (Saccharomyces) and pSV2neo (mammalian cells). See generally, "DNA Cloning": Vols. I & II, Glover et al. ed. IRL Press Oxford (1985) (1987); and T. Maniatis et al. ("Molecular Cloning" Cold Spring Harbor Laboratory (1982).

The gene can be placed under the control of control elements such as a promoter, ribosome binding site (for bacterial expression) and, optionally, an operator, so that the DNA sequence encoding the desired protein is transcribed into RNA in the host cell transformed by a vector containing the expression construct. The coding sequence may or may not contain a signal peptide or leader sequence. The proteins of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437 and 4,338,397.

In addition to control sequences, it may be desirable to add regulatory sequences which allow for regulation of the expression of the protein sequences relative to the growth of the host cell. Regulatory sequences are known to those of skill in the art. Exemplary are those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences, i.e., RNA polymerase which binds to the DNA molecule at the control sequences transcribes the coding sequence. Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogs of the NERF-1 and NERF-2 proteins. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; "DNA Cloning," Vols. I and II, supra; and "Nucleic Acid Hybridization", supra.

Depending on the expression system and host selected, the proteins of the present invention are produced by growing host cells transformed by an expression vector described above under conditions whereby the protein of interest is expressed. Preferred mammalian cells include human embryonic kidney cells, monkey kidney (HEK-293cells), fibroblast (COS) cells, Chinese hamster ovary (CHO) cells, Drosophila or murine L-cells. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to NERF-1 or NERF-2.

The proteins of the present invention may also be produced by chemical synthesis such as solid phase peptide synthesis on an automated peptide synthesizer, using known amino acid sequences or amino acid sequences derived from the DNA sequence of the genes of interest. Such methods are known to those skilled in the art.

Another aspect of the present invention is modulators of the polypeptides of the invention. Functional modulation of NERF by a substance includes partial to complete inhibition of function, identical function, as well as enhancement of function. Embodiments of modulators of the invention include antibodies, peptides, oligonucleotides and small organic molecules including peptidomimetics.

The proteins of the present invention or their fragments comprising at least one epitope can be used to produce antibodies, both polyclonal and monoclonal, directed to epitopes corresponding to amino acid sequences disclosed herein. If polyclonal antibodies are desired, a selected mammal such as a mouse, rabbit, goat or horse is immunized with a protein of the present invention, or its fragment, or a mutant protein. Serum from the immunized animal is collected and treated according to known procedures. Serum polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion and also by other techniques such as direct transformation of B lymphocytes with oncogenic DNA or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); and U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the antigen of interest, or fragment thereof, can be screened for various properties, i.e., for isotype, epitope, affinity, etc. Monoclonal antibodies are useful in purification, using immunoaffinity techniques, of the individual antigens which they are directed against. Alternatively, genes encoding the monoclonal of interest may be isolated from the hybridomas by PCR techniques known in the art and cloned and expressed in the appropriate vectors. The antibodies of this invention, whether polyclonal or monoclonal have additional utility in that they may be employed as reagents in immunoassays, RIA, ELISA, and the like. The antibodies of the invention can be labeled with an analytically detectable reagent such as a radioisotope, fluorescent molecule or enzyme.

Chimeric antibodies, in which non-human variable regions are joined or fused to human constant regions (see, e.g., Liu et al., *Proc. Natl Acad. Sci. USA*, 84, 3439 (1987)), may also be used in assays or therapeutically. Preferably, a therapeutic monoclonal antibody would be "humanized" as described in Jones et al., *Nature*, 321, 522 (1986); Verhoeyen et al., *Science*, 239, 1534 (1988); Kabat et al., *J. Immunol.*, 147, 1709 (1991); Queen et al., *Proc. Natl Acad. Sci. USA*, 86, 10029 (1989); Gorman et al., *Proc. Natl Acad. Sci. USA*, 88, 34181 (1991); and Hodgson et al., *Bio/Technology*, 9:, 421 (1991).

Another aspect of the invention is single-chain intracellular antibodies against NERF-1 or NERF-2, which may be used therapeutically to block the activity of NERF-1 or NERF-2.

Another aspect of the invention is antisense oligonucleotides comprising a sequence which is capable of binding to the polynucleotides of the invention. Synthetic oligonucleotides or related antisense chemical structural analogs can be designed to recognize and specifically bind to a target nucleic acid encoding NERF protein by those of ordinary skill in the art. See generally, Cohen, J. S., *Trends in Pharm. Sci.*, 10, 435(1989) and Weintraub, H. M., *Scientific American*, January (1990) at page 40.

Another aspect of the invention is double-stranded oligonucleotides comprising a sequence which is capable of binding to the polypeptides of the invention. Synthetic oligonucleotides or related antisense chemical structural analogs can be designed to recognize and specifically bind to the NERF proteins, in particular to the DNA binding domain, by those of ordinary skill in the art. These oligonucleotides may be used therapeutically to block binding of NERF proteins to their target DNA sequences.

Another aspect of the invention is a method for assaying a medium for the presence of a substance that inhibits or otherwise modulates NERF protein function by interfering with the binding of NERF protein to binding partners. A NERF protein is provided having the amino acid sequence of NERF-1 (SEQ ID NO:2) or NERF-2 (SEQ ID NO:4) or a functional derivative thereof together with a binding partner. The mixture is incubated with a test substance which is suspected of modulating NERF activity, under conditions which permit the formation of a NERF gene product/binding partner complex. An assay is performed for the presence of the complex, free NERF protein or free binding partner and the result compared to a control to determine the effect of the test substance.

The binding partner can be another protein, such as a cellular protein. NERF shows high homology in its DNA binding domain to the ets-related factor ELF-1. It is likely that the target genes regulated by NERF will be similar or identical to the genes regulated by ELF-1. An exemplary cellular binding partner is the retinoblastoma gene product. Thus, cellular binding partners are likely to include regulatory elements for HIV-2, HTLV-1, IL-2, IL-3, CD4, lck and GM-CSF transcription. NERF may play a role in regulation of these genes or viruses. Modulation of NERF function would be expected to have effects on HIV-2 or HTLV-1 replication and gene expression or on CD4 expression. Any modulators so identified would be expected to be useful as a therapeutic for AIDS and HTLV-1 induced leukemia. Involvement of NERF in the regulation of various T-cell cytokines such as IL-2, IL-3 and GM-CSF, as well as CD4 and lck, would render modulators of NERF function useful as modulators of T-cell function to either stimulate immune system activity for indications such as cancer, immunodeficiency diseases and infection or to suppress immune system activity for indications such as autoimmune diseases or organ transplantation.

Further, it is known that the amino terminus of NERF-2 contains a region of homology to ELF-1. See Example 2, infra. The homologous region in ELF-1 is involved in binding to the retinoblastoma gene product (RB), which is involved in the cell cycle and acts as a tumor suppressor gene. Accordingly, NERF-2 may bind to RB and exert cell cycle and tumor suppressor effects.

NERF-1 does not contain the ELF-1 RB binding homology region. Also, it is known that NERF transcripts are expressed to different extents in different tissues. See Example 2, infra. While the applicant does not wish to be bound to any theory, the ratio of NERF-1 to NERF-2 in a particular cell may be important for cell cycle control or proliferation. Modulation of the function or expression of NERF-1 or NERF-2 may be useful to shift the balance in one direction or the other and may be desirable under certain circumstances.

Additionally, NERF protein contains various potential phosphorylation sites for different protein kinases involved in signal transduction including tyrosine kinases, MAP kinase, kinase C, jun kinase and cAMP dependent kinase. Since it is known that the majority of ets-related factors are involved in growth regulation and differentiation of cells and are regulated by all of the major signal transduction pathways, NERF function is likely to also be regulated by various cytokines and growth factors. Specific inhibitors or activators of kinases or phosphatases involved in modulation of NERF protein activity may be useful for therapeutic use to block or induce NERF function. Some transcription factors have been shown to be phosphorylated by very specific kinases. NERF could be used to isolate kinases or phosphatases which phosphorylate or dephosphorylate it and these kinases or phosphatases could be a target for interference.

Further, most, if not all, ets-related factors interact with specific transcription factors of other transcription factor families. NERF could be used to isolate proteins which interact with it and this interaction could be a target for interference. Inhibitors of protein-protein interactions between NERF and other factors could lead to the development of pharmaceutical agents for the modulation of NERF activity.

Methods to assay for protein-protein interactions, such as that of a NERF gene product/binding partner complex, and to isolate proteins interacting with NERF are known to those skilled in the art. Use of the methods discussed below enable one of ordinary skill in the art to accomplish these aims without undue experimentation.

The yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech. Briefly, NERF cDNA is fused to a Ga14 transcription factor DNA binding domain and expressed in yeast cells. cDNA library members obtained from cells of interest are fused to a transactivation domain of Ga14. cDNA clones which express proteins which can interact with NERF will lead to reconstitution of Ga14 activity and transactivation of expression of a reporter gene such as Ga11-lacZ.

An alternative method is screening of λgt11 cDNA expression libraries with recombinant NERF. Recombinant NERF protein or fragments thereof are fused to small peptide tags such as FLAG, HSV or GST. The peptide tags can possess convenient phosphorylation sites for a kinase such as heart muscle creatine kinase or they can be biotinylated. Recombinant NERF can be phosphorylated with $^{32}[p]$ or used unlabeled and detected with streptavidin or antibodies against the tags. λgt11cDNA expression libraries are made from cells of interest and are incubated with the recombinant NERF, washed and cDNA clones isolated which interact with NERF. Another alternative method is isolation of proteins interacting with NERF directly from cells. Fusion proteins of NERF with GST or small peptide tags are made and immobilized on beads. Biosynthetically labeled or unlabeled protein extracts from the cells of interest are prepared, incubated with the beads and washed with buffer. Proteins interacting with NERF are eluted specifically from the beads and analyzed by SDS-PAGE. Binding partner primary amino acid sequence data are obtained by microsequencing.

Another alternative method is immunoaffinity purification. Recombinant NERF is incubated with labeled or unlabeled cell extracts and immunoprecipitated with anti-NERF antibodies. The immunoprecipitate is recovered with protein A-Sepharose and analyzed by SDS-PAGE. Unlabelled proteins are labeled by biotinylation and detected on SDS gels with streptavidin. Binding partner proteins will be analyzed by microsequencing.

Another alternative method is isolation of proteins which interact with NERF only in the presence of a specific DNA sequence. Recombinant NERF is labeled or biotinylated and incubated with nuclear or cytoplasmic extracts derived from the cells of interest in the presence of oligonucleotides containing a NERF binding site and a binding site for a protein which forms heterodimers with NERF. Protein-DNA complexes are separated either by electrophoretic mobility shift assays or on streptavidin-magnetic beads. Proteins interacting with NERF are separated by SDS-PAGE and microsequenced.

Yet another alternative method is screening of peptide libraries for binding partners. Recombinant tagged or labeled NERF is used to select peptides from a peptide library which interact with NERF. Sequencing of the peptides leads to identification of consensus peptide sequences which might be found in interacting proteins.

NERF binding partners identified by any of these methods or other methods which would be known to those of ordinary skill in the art as well as those putative binding partners discussed above can be used in the assay method of the invention. Assaying for the presence of NERF/binding partner complex are accomplished by, for example, the yeast two-hybrid system, ELISA or immunoassays using antibodies specific for the complex. In the presence of test substances which interrupt or inhibit formation of NERF/binding partner interaction, a decreased amount of complex will be determined relative to a control lacking the test substance.

Assays for free NERF or binding partner are accomplished by, for example, ELISA or immunoassay using specific antibodies. In the presence of test substances which interrupt or inhibit formation of NERF/binding partner interaction, an increased amount of free NERF or free binding partner will be determined relative to a control lacking the test substance.

Another aspect of the invention is pharmaceutical compositions comprising an effective amount of the NERF-1 and/or NERF-2 protein of the invention and a pharmaceutically acceptable carrier. Pharmaceutical compositions of proteinaceous drugs of this invention are particularly useful for parenteral administration, i.e., subcutaneously, intramuscularly or intravenously. Optionally, the NERF protein is surrounded by a membrane bound vesicle, such as a liposome.

The compositions for parenteral administration will commonly comprise a solution of the proteins of the invention or a cocktail thereof dissolved in an acceptable carrier, preferably an aqueous carrier. A variety of aqueous carriers may be employed, e.g., water, buffered water, 0.4% saline, 0.3% glycine and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the protein of the invention in such pharmaceutical formulation can very widely, i.e., from less than about 0.5%, usually at or at least about 1% to as much as 15 or 20% by weight and will be selected primarily based on fluid volumes, viscosities, etc. according to the particular mode of administration selected.

Thus, a pharmaceutical composition of the invention for intramuscular injection could be prepared to contain 1 mL sterile buffered water, and 50 mg of a protein of the invention. Similarly, a pharmaceutical composition of the invention for intravenous infusion could be made up to contain 250 ml of sterile Ringer's solution, and 150 mg of a protein of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The proteins described herein can be lyophilized for storage and reconstituted in a suitable carrier prior to use. This technique has been shown to be effective with conventional proteins and art-known lyophilization and reconstitution techniques can be employed.

The physician will determine the dosage of the present therapeutic agents which will be most suitable and it will vary with the form of administration and the particular compound chosen, and furthermore, it will vary with the particular patient under treatment. Generally, the physician will wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The therapeutic dosage will generally be from 1 to 10 milligrams per day and higher although it may be administered in several different dosage units.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance to the disease.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

NERF, by homology, has been shown to be a member of the ets family of transcription factors, a class of genes involved in the development of human cancers such as Ewing's sarcoma, chronic myelogenous leukemeia and acute myelogenous leukemia. See Example 2, infra. Accordingly, another aspect of the invention is the use of the NERF gene as a diagnostic for certain human diseases. Most ets-related genes which have been found to be involved in human tumor formation are involved in specific chromosomal translocations leading to the expression of distinct fusion proteins. Chromosomal analysis of the NERF gene will help to determine whether NERF is located at a potential hot spot for chromosome translocation. Any fusion protein derived from a specific chromosome translocation involving NERF would be a potential therapeutic target. Approaches to interfere with such a fusion protein might involve any step between gene transcription to the functioning of the fusion protein.

Additionally, some diseases result from inherited defective genes. These genes can be detected by comparing the sequence of the defective gene with that of a normal one. Individuals carrying mutations in the NERF genes may be detected at the DNA level by a variety of techniques. Nucleic acids used for diagnosis (genomic DNA, mRNA, etc.) may be obtained from a patient's cells, such as from blood, urine, saliva or tissue biopsy, e.g., chorionic villi sampling or removal of amniotic fluid cells and autopsy material. The genomic DNA may be used directly for detection or may be amplified enzymatically by using PCR, ligase chain reaction (LCR), strand displacement amplifcation (SDA), etc. prior to analysis. See, e.g., Saiki et al., Nature, 324, 163–166 (1986), Bej, et al., Crit. Rev. Biochem. Molec. Biol., 26, 301–334 (1991), Birkenmeyer et al., J. Virol. Meth., 35, 117–126 (1991), Van Brunt, J., Bio/Technology, 8, 291–294 (1990)). RNA or cDNA my also be used for the same purpose. As an example, PCR primers complementary to the nucleic acid of the instant invention can be used to identify and analyze NERF mutations. For example, deletions and insertions can be detected by a change in size of the amplified product in comparison to the normal NERF genotype. Point mutations can be identified by hybridizing amplified DNA to rabiolabeled NERF RNA of the invention or alternatively, radiolabelled NERF antisense DNA sequences of the invention. Perfectly matched sequences can be distinguished from mismatched duplexes by RNase A digestion or by differences in melting temperatures (Tm). Such a diagnostic would be particularly useful for prenatal and even neonatal testing.

In addition, point mutations and other sequence differences between the reference gene and "mutant" genes can be identified by yet other well-known techniques, e.g., direct DNA sequencing, single-strand conformational polymorphism. See Orita et al., Genomics, 5, 874–879 (1989). For example, a sequencing primer is used with double-stranded PCR product or a single-stranded template molecule generated by a modified PCR. The sequence determination is performed by conventional procedures with radiolabeled nucleotides or by automatic sequencing procedures with fluorescent-tags. Cloned DNA segments may also be used as probes to detect specific DNA segments. The sensitivity of this method is greatly enhanced when combined with PCR. The presence of nucleotide repeats may correlate to a causative change in NERF activity or serve as marker for various polymorphisms.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures. See, e.g., Myers et al., Science, 230, 1242 (1985). In addition, sequence alterations, in particular small deletions, may be detected as changes in the migration pattern of DNA heteroduplexes in non-denaturing gel electrophoresis such as heteroduplex electrophoresis. See, e.g., Nagamine et al., Am. J. Hum. Genet., 45, 337–339 (1989). Sequence changes at specific locations may also be revealed by nuclease protection assays, such as RNase and S1 protection or the chemical cleavage method as disclosed by Cotton et al. in Proc. Natl. Acad. Sci. USA, 85, 4397–4401 (1985).

Thus, the detection of a specific DNA sequence may be achieved by methods such as hybridization (e.g., heteroduplex electroporation, see, White et al., Genomics, 12, 301–306 (1992), RNAse protection (e.g., Myers et al., Science, 230, 1242 (1985)) chemical cleavage (e.g., Cotton et al., Proc. Natl. Acad. Sci. USA, 85, 4397–4401 (1985))), direct DNA sequencing, or the use of restriction enzymes (e.g., restriction fragment length polymorphisms (RFLP) in which variations in the number and size of restriction fragments can indicate insertions, deletions, presence of nucleotide repeats and any other mutation which creates or destroys an endonuclease restriction sequence). Southen blotting of genomic DNA may also be used to identify large (i.e., greater than 100 base pair) deletions and insertions.

In addition to conventional gel electrophoresis and DNA sequencing, mutations such as microdeletions, aneuploidies, translocations, inversions, can also be detected by in situ analysis. See, e.g., Keller et al., DNA Probes, 2nd Ed., Stockton Press, New York, N.Y., USA (1993). That is, DNA or RNA sequences in cells can be analyzed for mutations without isolation and/or immobilization onto a membrane. Fluorescence in situ hybridization (FISH) is presently the most commonly applied method and numerous reviews of FISH have appeared. See, e.g., Trachuck et al., Science, 250, 559–562 (1990), and Trask et al., Trends, Genet., 7, 149–154 (1991). Hence, by using nucleic acids based on the structure of the NERF genes, one can develop diagnostic tests for genetic mutations.

In addition, some diseases are a result of, or are characterized by, changes in gene expression which can be detected by changes in the mRNA. Alternatively, the NERF genes can be used as a reference to identify individuals expressing a decreased level of NERF-1 or NERF-2 protein, e.g., by Northern blotting or in situ hybridization.

Defining appropriate hybridization conditions is within the skill of the art. See, e.g., "Current Protocols in Mol. Biol." Vol. I & II, Wiley Interscience, Ausbel et al. (eds.) (1992). Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioisotopes, fluorescent dyes or enzymes capable of catalyzing the formation of a detectable product. As a general rule, the more stringent the hybridization conditions the more closely related genes will be that are recovered.

The putative role of NERF in cancer development establishes yet another aspect of the invention which is gene therapy. "Gene therapy" means gene supplementation where an additional reference copy of a gene of interest is inserted into a patient's cells. As a result, the protein encoded by the reference gene corrects the defect and permits the cells to function normally, thus alleviating disease symptoms. The reference copy would be a wild-type form of the NERF gene or a gene encoding a protein or peptide which modulates the activity of the endogenous NERF.

Gene therapy of the present invention can occur in vivo or ex vivo. Ex vivo gene therapy requires the isolation and purification of patient cells, the introduction of a therapeutic gene and introduction of the genetically altered cells back into the patient. A replication-deficient virus such as a modified retrovirus can be used to introduce the therapeutic NERF gene into such cells. For example, mouse Moloney leukemia virus (MMLV) is a well-known vector in clinical gene therapy trials. See, e.g., Boris-Lauerie et al., *Curr. Opin. Genet. Der.*, 3, 102–109 (1993).

In contrast, in vivo gene therapy does not require isolation and purification of a patient's cells. The therapeutic gene is typically "packaged" for administration to a patient such as in liposomes or in a replication-deficient virus such as adenovirus as described by Berkner, K. L., in *Curr. Top. Microbiol. Immunol.*, 158, 39–66 (1992) or adeno-associated virus (AAV) vectors as described by Muzyczka, N., in *Curr. Top. Microbiol. Immunol.*, 158, 97–129 (1992) and U.S. Pat. No. 5,252,479. Another approach is administration of "naked DNA" in which the therapeutic gene is directly injected into the bloodstream or muscle tissue. Another approach is administration of "naked DNA" in which the therapeutic gene is introduced into the target tissue by microparticle bombardment using gold particles coated with the DNA.

Cell types useful for gene therapy of the present invention include hepatocytes, myoblasts, fibroblasts, lymphocytes, any cell of the eye such as retinal cells, epithelial and endothelial cells. Preferably the cells are hepatocytes, any cell of the eye or respiratory or pulmonary epithelial cells. Transfection of pulmonary epithelial cells can occur via inhalation of a neubulized preparation of DNA vectors in liposomes, DNA-protein complexes or replication-deficient adenoviruses. See, e.g., U.S. Pat. No. 5,240,846.

Another aspect of the invention is transgenic, non-human mammals capable of expressing the polynucleotides of the invention in any cell. Transgenic, non-human animals may be obtained by transfecting appropriate fertilized eggs or embryos of a host with the polynucleotides of the invention or with mutant forms found in human diseases. See, e.g., U.S. Pat. Nos. 4,736,866; 5,175,385; 5,175,384 and 5,175,386. The resultant transgenic animal may be used as a model for the study of NERF gene function. Particularly useful transgenic animals are those which display a detectable phenotype associated with the expression of the NERF-1 or NERF-2 protein. Drug development candidates may then be screened for their ability to reverse or exacerbate the relevant phenotype.

Another aspect of this invention is the operative linking of the polynucleotides of the invention to regulatory elements which are differentially responsive to various temperature or metabolic conditions, thereby effectively turning on or off the phenotypic expression in response to those conditions.

The present invention will now be described with reference to the following specific, non-limiting examples.

EXAMPLE 1

Cloning of NERF-1 and NERF-2 full-length cDNA and Sequence Analysis

A partial cDNA having homology to a murine ets-related protein was isolated from a human brain cDNA library and designated new ets-related factor (NERF). Human spleen and fetal liver cDNA ready for 5' rapid amplification of cDNA ends primer extension (5'-RACE) was obtained from Clontech and 5'-RACE polymerase chain reaction (PCR) amplification was performed according to the manufacturer using a 5' anchor primer having the sequence 5'-CTGGTTCGGCCCACCTCTGAAGGTTCCAGAATC-GATAG-3' (SEQ ID NO:5) and nested primers specific for the 5' end of the partial cDNA having the sequences 5'-AGAGACAGCCTTTGAATCCACCAGC-3' and 5'-CTCAGGAGACCCATTGGAAATTGGTG-3' (SEQ ID NOS:6 and 7, respectively).

5' RACE PCR amplifications were carried out in a final volume of 50 ul containing 100 ng of 5'RACE-cDNA, 50 mM KCl, 10 mM Tris-HCl (pH 8.3), 2 mM $MgCl_2$, 0.2 mM deoxynucleoside triphosphates and 0.5 ul of Taq DNA polymerase (Promega), 10 pmol of the anchor primer (SEQ ID NO:5) with either 10 pmol of SEQ ID NO:6 or SEQ ID NO:7. Reaction mixtures were overlaid with mineral oil and amplified by using a Perkin-Elmer Cetus thermal cycler 480 as follows: 30 cycles of 45s at 94° C. 45s at 60° C. and 2 min at 72° C. followed by 7 min at 72° C. After two rounds of PCR amplification, ten ul of the reaction products were analyzed on 2% agarose gels. 40 ul of the relevant amplified DNA fragments were subcloned into the TA cloning vector obtained from Invitrogen. Colonies of recombinant clones were randomly picked and minipreparations of plasmid DNA was prepared using the Wizard Miniprep Kit from Promega. The isolated plasmid DNA was digested with EcoRI and analyzed on a 0.8% agarose gel. Double-stranded cDNA inserts of varying lengths present in plasmid preparations from several different PCR amplifications were sequenced on an Applied Biosystems automatic DNA sequencer Model 373A using the Taq DyeDeoxy Terminator Cycle Sequencing Kit__ and a combination of specific oligonucleotide primers.

All of the clones sequenced contained NERF-specific cDNAs of varying lengths which extended toward the 5' end. Two alternative splice products of NERF, NERF-1 and NERF-2, which differed in their 5' end sequence, were identified. The 5' end sequence of the NERF cDNAs was confirmed by repeating 5'-RACE PCR amplification using primers specific for the 5' end of the longest 5'-RACE products obtained in the first two rounds of PCR amplification. These primers have the sequence 5'-CGGATGAGCAGATCCAGCTGGTTCG-3' (SEQ ID NO:8) and 5'-CCTGCTCTAATCTGGCACTTGGAAC-3' (SEQ ID NO:9). Sequencing of the PCR products confirmed the apparent 5' ends of NERF-1 and NERF-2. The length of the NERF-1 full length cDNA is 2975 bp and that of NERF-2 is 3240 bp. These data correlate well with the estimated sizes of the two mRNA species detected by Northern blot analysis. See example 2, infra.

Sequence analysis of the NERF-1 cDNA revealed a 1,563 nucleotide open reading frame encoding a 521 amino acid protein with a predicted molecular mass of 57.3 kDa, starting with an ATG at position 122 and terminating with a TAA at position 1685.

Sequence analysis of the NERF-2 cDNA revealed a 1,743 nucleotide open reading frame encoding a 581 amino acid protein with a predicted molecular mass of 64 kDa, starting with an ATG at position 207 and terminating with a TAA at position 1950.

Comparison of the deduced amino acid sequence of NERF with other members of the ets family revealed the highest homology to ELF-1. Homologies were clustered in several primary regions, the putative DNA binding domain (ETS domain) which extends over approximately 85 amino acids in the middle of the gene, a smaller basic domain just upstream of the ETS domain and several shorter, mostly acidic stretches of homology further towards the amino terminus. The NERF-2 gene product contained additional short stretches of homology to ELF-1 at the amino terminus which are not present in NERF-1. The region towards the carboxy terminus of NERF showed only limited homology to ELF-1.

EXAMPLE 2

Northern Blot Analysis of NERF mRNA

Poly(A)$^+$ mRNAs were isolated from approximately $10^8$ cells and Northern blots made using 3 ug of poly(A)$^+$ selected mRNA as described by Libermann et al. in *EMBO J.* 6, 1627–1632 (1987). Northern blots containing poly(A)$^+$ selected mRNA derived from different human tissues were obtained from Clontech. Northern blots were hybridized with $2 \times 10^6$ cpm/ml of random prime-labeled NERF cDNA fragment at 42° C. for 1 h in QuickHyb solution (Stratagene) containing 200 mg/ml salmon sperm DNA. After washing at 68_C with 0.2x SSC, 0.2% SDS, the filters were autoradiographed for 2 days at -70° C using intensifier screens.

To determine the expression pattern of NERF and the size of the NERF transcripts, poly(A)$^+$ mRNA derived from various human tissues were analyzed by Northern blot hybridization using NERF cDNA as a probe. To control for RNA quality and quantity, we rehybridized the Northern blots with a β-actin probe.

The results indicated the presence of at least two predominant NERF transcripts of approximately 3 kb and 3.3 kb. Further, it was found that the NERF gene was expressed in all tissues tested with significant variation in abundance. In human fetal tissues, heart expressed the highest amounts of NERF. Moderate levels of NERF were found in lung, kidney and liver. Very low levels of NERF mRNA were observed in brain. The 3 and 3.3 kb transcripts were expressed in most tissues in approximately equivalent amounts, except in brain where the 3.3 kb transcript was predominant. In adult tissues, testes, ovary and skeletal muscle expressed the highest levels of NERF. Moderate levels of NERF transcripts were found in spleen, thymus, prostate, small intestine, heart, kidney, lung and liver. Lower levels of NERF mRNA were expressed in colon, brain, pancreas and placenta. The 3 and 3.3 kb transcripts were expressed only in heart, lung, liver, and skeletal muscle in approximately equivalent amounts. The 3.3 kb transcript was predominant in testes and brain, whereas the 3 kb transcript was more abundant in ovary, spleen, thymus, prostate, small intestine, colon, pancreas and placenta.

The results suggest that NERF is expressed to varying degrees in many tissues. NERF-1 cDNA appears to be derived from the 3 kb transcript, whereas NERF-2 cDNA is derived from the 3.3 kb transcript. The different transcripts appear to be due to alternative splicing.

The present invention may be embodied in other specific forms without departing from the spirit or essential attributes thereof, and, accordingly, reference should be made to the appended claims, rather than to the foregoing specfication, as indicating the scope of the invention.

---

We claim:

1. An isolated polynucleotide encoding a polypeptide having transcriptional regulatory activity selected from the group consisting of:
    (a) a polynucleotide encoding NERF-1 having the nucleotide sequence as set forth in SEQ ID NO: 1 from nucleotide 122 to 1684;
    (b) a polynucleotide which hybridizes to the complement of a polynucleotide according to (a) and is about 90% identical; and
    (c) a degenerate polynucleotide according to (a) or (b).

2. An isolated polynucleotide encoding a polypeptide having transcriptional regulatory activity selected from the group consisting of:
    (a) a polynucleotide encoding NERF-2 having the nucleotide sequence as set forth in SEQ ID NO: 3 from nucleotide 207 to 1949;
    (b) a polynucleotide which hybridizes to the complement of a pollnucleotide according to (a) and is about 90% identical; and
    (c) a degenerate polynucleotide according to (a) or (b).

3. An isolated polynucleotide having the nucleotide sequence as set forth in SEQ ID NO:1.

4. An isolated polynucleotide having the nucleotide sequence as set forth in SEQ ID NO:3.

5. The polynucleotide of claim 1 or 2 which is DNA.

6. The polynucleotide of claim 1 or 2 which is RNA.

7. The polynucleotide of claim 1 or 2 which is of human origin.

8. A vector comprising the DNA of claim 5.

9. A recombinant host cell comprising the vector of claim 8.

10. A method for preparing essentially pure NERF-1 or NERF-2 protein comprising culturing the recombinant host cell of claim 9 under conditions promoting expression of the protein and recovery thereof.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2975 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GTGGTGAGTG  TGTGTCGGTC  GCACGGCGTG  TGTCTCCGGC  CGCGGGTTCC  GCCTCCTCCC      60

CTGCCGCCGC  TGCTCACGGT  GTAAGTCAAT  GTGAAGCAGC  AGCTCCAGCC  CCGGGATAAA     120

CATGGCGACG  TCTCTGCATG  AGGGACCCAC  GAACCAGCTG  GATCTGCTCA  TCCGGGCCGT     180
```

```
GGAAGCATCA GTTCACAGCA GTAATGCACA CTGTACAGAT AAGACAATTG AAGCTGCTGA      240
AGCCCTGCTT CATATGGAAT CTCCTACCTG CTTGAGGGAT TCAAGAAGTC CTGAATTCAT      300
CCATGCTGCT ATGAGGCCAG ATGTCATTAC AGAAACTGTA GTGGAGGTGT CAACTGAAGA      360
GTCTGAACCC ATGGATACCT CTCCTATTCC AACATCACCA GATAGCCATG AACCAATGAA      420
AAAGAAAAAA GTTGGCCGTA AACCAAAGAC CCAGCAATCA CCAATTTCCA ATGGGTCTCC      480
TGAGTTAGGT ATAAAGAAGA AACCAAGAGA AGGAAAAGGA AACACAACCT ATTTGTGGGA      540
GTTTCTTTTA GATCTACTTC AAGATAAAAA TACTTGTCCC AGGTATATTA AATGGACTCA      600
GAGAGAAAAA GGCATATTCA AGCTGGTGGA TTCAAAGGCT GTCTCTAAGC TTTGGGAAA       660
GCATAAGAAC AAACCAGACA TGAACTATGA AACCATGGGA CGAGCTTTGA GATACTACTA      720
CCAAAGGGGA ATTCTTGCAA AGGTTGAAGG ACAGAGGCTT GTATATCAGT TCAAGGATAT      780
GCCGAAAAAC ATAGTGGTCA TAGATGATGA CAAAAGTGAA ACCTGTAATG AAGATTTAGC      840
AGGAACTACT GATGAAAAAT CATTAGAACG AGTGTCACTG TCTGCAGAAA GTCTCCTGAA      900
AGCAGCATCC TCTGTTCGCA GTGGAAAAAA TTCATCCCCT ATAAACTGCT CCAGAGCAGA      960
GAAGGGTGTA GCTAGAGTTG TGAATATCAC TTCCCCTGGG CACGATGCTT CATCCAGGTC     1020
TCCTACTACC ACTGCATCTG TGTCAGCAAC AGCAGCTCCA AGGACAGTTC GTGTGGCAAT     1080
GCAGGTACCT GTTGTAATGA CATCATTGGG TCAGAAAATT TCAACTGTGG CAGTTCAGTC     1140
AGTTAATGCA GGTGCACCAT TAATAACCAG CACTAGTCCA ACAACAGCGA CCTCTCCAAA     1200
GGTAGTCATT CAGACAATCC CTACTGTGAT GCCAGCTTCT ACTGAAAATG GAGACAAAAT     1260
CACCATGCAG CCTGCCAAAA TTATTACCAT CCCAGCTACA CAGCTTGCAC AGTGTCAACT     1320
GCAGACAAAG TCAAATCTGA CTGGATCAGG AAGCATTAAC ATTGTTGGAA CCCCATTGGC     1380
TGTGAGAGCA CTTACCCCTG TTTCAATAGC CCATGGTACA CCTGTAATGA GACTATCAAT     1440
GCCTACTCAG CAGGCATCTG GCCAGACTCC TCCTCGAGTT ATCAGTGCAG TCATAAAGGG     1500
GGCAGAGGTT AAATCGGAAG CAGTGGCAAA AAAGCAAGAA CATGATGTGA AAACTTTGGA     1560
GCTAGTAGAA GAAAAACCAG CAGATGGAAA TAAGACAGTG ACCCACGTAG TGGTTGTCAG     1620
TGCGCCTTCA GCTATTGCCC TTCCTGTAAC TATGAAAACA GAAGGACTAG TGACATGTGA     1680
GAAATAAAAT AGCAGCTCCA CCATGGACTT CAGGCTGTTA GTGGCAGTAC TGACATAAAC     1740
ATTTGCAAGG GAAGTCATCA AGAAAAGTCC AAAGAAGACT TTAAAACATT TTAATGCAT      1800
ATACAAAAAC AATCAGACTT ACTGGAAATA AATTACCTAT CCCATGTTTC AGTGGGAAAT     1860
GAACTACATA TTGAGATGCT GACAGAAAAC TGCCTCTTAC AGTAGGAAAC AACTGAACCC     1920
ATCAATAAGA AAAAGGATCG AAAGGGACCA AGCAGCTCAC TACGATATCA AGTTACACTA     1980
AGACTTGGAA CACTAACATT CTGTAAGAGG TTATATAGTT TTTCAGTGGG AGGGGTTGGG     2040
ATGGGTAATC TCATTGTTAC ATATAGCAAT TTTTGATGCA TTTTATATGC ATACCAGCAA     2100
TTATTACTGT GTTCGCACAG TTCTCACTTA ACTGGTGCTA TGTGAAGACT CTGCTAATAT     2160
AGGTATTTTA GAATGTGAAT TGAAGAATGG ATCCCAAAAA CTTCAGAAAG AGGATAGCAA     2220
AAAAAGATCT AGTGCGATTT TATATATATA TATATATATA TATACATACA TATATATATA     2280
TCATATAGCT TAAGCTGATT TAAAACAAAG GCCTTAGACT AATTTTCGAT TTTCTTTCTT     2340
GAAATAAGCT AATGGCTTGT TTGTGTAAAG CTTTTTTATT AAAAGAAAAA TTTTAAAAAT     2400
CTTGTACCTA GCACAGTATT GTTATAGAAT ATACATGTAA CATTTTATAT GGTAGTTTAA     2460
GTCTGTCAGT TTCTTAATTG TGGACAAATT AACAGTTGGC TCTGGCCTTT TGCTGTAACA     2520
TGCCTGTGTC ACTCACTTAG CCTTGGCATT TGTGCAGACA TACCATTTTC AGTTCTGCTG     2580
```

```
TCACTTGGAA GTTCAGGCTC AGCATGAATT TTTGGCAGGT AGCTCTAATA CCTGGAGTTT      2640

TCTTTGTTTT TTTTCTTTT  TTTTAGTTGA AGTTTATGAG GGAAATACCA GTGTTCAGTT      2700

TTGAACTATA ATAGTTTGTA TATTCAACAT TTGAAGTATA TTCTATTTTG TTGTACTCTT      2760

GTTTCAAAGT GTATTCAAGT AGGTTTTCTG AAATATAGAA ATGAAATTTA TCTTCTGTTT      2820

TGGTCTCTGG TGATATTTTA AACAATATTT AAAAGTCAGT ATAGAAGTGT TTTAGTTAGG      2880

AAGTGATAAA ACATCTCTCT TCTCCTTCCC AACTACTGCA TGAAGAAATT CTACTTCCAT      2940

TATATTAATA TTTGGGCAAA AAAAAAAAAA AAAAA                                 2975
```

( 2 ) INFORMATION FOR SEQ ID NO:2:

( i ) SEQUENCE CHARACTERISTICS:
     ( A ) LENGTH: 521 amino acids
     ( B ) TYPE: amino acid
     ( D ) TOPOLOGY: linear ( i i ) MOLECULE TYPE: protein ( x i ) SEQUENCE DESCRIPTION: SEQ ID NO:2:

```
Met Ala Thr Ser Leu His Glu Gly Pro Thr Asn Gln Leu Asp Leu Leu
 1               5                  10                  15

Ile Arg Ala Val Glu Ala Ser Val His Ser Ser Asn Ala His Cys Thr
            20                  25                  30

Asp Lys Thr Ile Glu Ala Ala Glu Ala Leu Leu His Met Glu Ser Pro
        35                  40                  45

Thr Cys Leu Arg Asp Ser Arg Ser Pro Glu Phe Ile His Ala Ala Met
    50                  55                  60

Arg Pro Asp Val Ile Thr Glu Thr Val Val Glu Val Ser Thr Glu Glu
65                  70                  75                  80

Ser Glu Pro Met Asp Thr Ser Pro Ile Pro Thr Ser Pro Asp Ser His
                85                  90                  95

Glu Pro Met Lys Lys Lys Val Gly Arg Lys Pro Lys Thr Gln Gln
           100                 105                 110

Ser Pro Ile Ser Asn Gly Ser Pro Glu Leu Gly Ile Lys Lys Lys Pro
       115                 120                 125

Arg Glu Gly Lys Gly Asn Thr Thr Tyr Leu Trp Glu Phe Leu Leu Asp
   130                 135                 140

Leu Leu Gln Asp Lys Asn Thr Cys Pro Arg Tyr Ile Lys Trp Thr Gln
145                 150                 155                 160

Arg Glu Lys Gly Ile Phe Lys Leu Val Asp Ser Lys Ala Val Ser Lys
                165                 170                 175

Leu Trp Gly Lys His Lys Asn Lys Pro Asp Met Asn Tyr Glu Thr Met
            180                 185                 190

Gly Arg Ala Leu Arg Tyr Tyr Tyr Gln Arg Gly Ile Leu Ala Lys Val
        195                 200                 205

Glu Gly Gln Arg Leu Val Tyr Gln Phe Lys Asp Met Pro Lys Asn Ile
    210                 215                 220

Val Val Ile Asp Asp Lys Ser Glu Thr Cys Asn Glu Asp Leu Ala
225                 230                 235                 240

Gly Thr Thr Asp Glu Lys Ser Leu Glu Arg Val Ser Leu Ser Ala Glu
                245                 250                 255

Ser Leu Leu Lys Ala Ala Ser Ser Val Arg Ser Gly Lys Asn Ser Ser
            260                 265                 270

Pro Ile Asn Cys Ser Arg Ala Glu Lys Gly Val Ala Arg Val Val Asn
       275                 280                 285
```

| | | | | | | | | | | | | | | |
|---|---|---|---|---|---|---|---|---|---|---|---|---|---|---|
| Ile | Thr 290 | Ser | Pro | Gly | His 295 | Asp | Ala | Ser | Ser | Arg 300 | Ser | Pro | Thr | Thr | Thr |
| Ala 305 | Ser | Val | Ser | Ala | Thr 310 | Ala | Ala | Pro | Arg | Thr 315 | Val | Arg | Val | Ala | Met 320 |
| Gln | Val | Pro | Val | Val 325 | Met | Thr | Ser | Leu | Gly 330 | Gln | Lys | Ile | Ser | Thr 335 | Val |
| Ala | Val | Gln | Ser 340 | Val | Asn | Ala | Gly | Ala 345 | Pro | Leu | Ile | Thr | Ser 350 | Thr | Ser |
| Pro | Thr | Thr 355 | Ala | Thr | Ser | Pro | Lys 360 | Val | Val | Ile | Gln | Thr 365 | Ile | Pro | Thr |
| Val | Met 370 | Pro | Ala | Ser | Thr | Glu 375 | Asn | Gly | Asp | Lys | Ile 380 | Thr | Met | Gln | Pro |
| Ala 385 | Lys | Ile | Ile | Thr | Ile 390 | Pro | Ala | Thr | Gln | Leu 395 | Ala | Gln | Cys | Gln | Leu 400 |
| Gln | Thr | Lys | Ser | Asn 405 | Leu | Thr | Gly | Ser | Gly 410 | Ser | Ile | Asn | Ile | Val 415 | Gly |
| Thr | Pro | Leu | Ala 420 | Val | Arg | Ala | Leu | Thr 425 | Pro | Val | Ser | Ile | Ala 430 | His | Gly |
| Thr | Pro | Val 435 | Met | Arg | Leu | Ser | Met 440 | Pro | Thr | Gln | Gln | Ala 445 | Ser | Gly | Gln |
| Thr | Pro 450 | Pro | Arg | Val | Ile | Ser 455 | Ala | Val | Ile | Lys | Gly 460 | Ala | Glu | Val | Lys |
| Ser 465 | Glu | Ala | Val | Ala | Lys 470 | Lys | Gln | Glu | His | Asp 475 | Val | Lys | Thr | Leu | Glu 480 |
| Leu | Val | Glu | Glu | Lys 485 | Pro | Ala | Asp | Gly | Asn 490 | Lys | Thr | Val | Thr | His 495 | Val |
| Val | Val | Val | Ser 500 | Ala | Pro | Ser | Ala | Ile 505 | Ala | Leu | Pro | Val | Thr 510 | Met | Lys |
| Thr | Glu | Gly | Leu | Val 515 | Thr | Cys | Glu 520 | Lys | | | | | | | |

( 2 ) INFORMATION FOR SEQ ID NO:3:

( i ) SEQUENCE CHARACTERISTICS:
    ( A ) LENGTH: 3240 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:3:

```
GTGTTAGTGA AGGATGCTTA GACTACTTAA CATACAAACT GCTTTCTGGT TAATCATCTT      60
TAGAAGACTG GATTTCTGGA TATCTACTCC ACTCCATCTC TATTGACCTT TAAAACATGA     120
TAGTGCAAAC CTATAACACT GGCAACCATC AGTGAACCTT TAATTTCATT GATTAATAGC     180
GTTTGAAGCT TCCTCAGGGA ATAACAATGA CATCAGCAGT GGTTGACAGT GGAGGTACTA     240
TTTTGGAGCT TTCCAGCAAT GGAGTAGAAA ATCAAGAGGA AAGTGATAAG GTTTCTGAAT     300
ATCCAGCAGT GATTGTGGAG CCAGTTCCAA GTGCCAGATT AGAGCAGGGG TATGCAGCCC     360
AGGTTCTGGG TTATGATGAT GAGACTTATT TGATGCAAGA TGTGGCAGAA GAACAAGAAG     420
TTGAGACCGA GAATGCGGAA ACAGTGGAAG CATCAGTTCA CAGCAGTAAT GCACACTGTA     480
CAGATAAGAC AATTGAAGCT GCTGAAGCCC TGCTTCATAT GGAATCTCCT ACCTGCTTGA     540
GGGATTCAAG AAGTCCTGAA TTCATCCATG CTGCTATGAG GCCAGATGTC ATTACAGAAA     600
CTGTAGTGGA GGTGTCAACT GAAGAGTCTG AACCCATGGA TACCTCTCCT ATTCCAACAT     660
```

```
CACCAGATAG CCATGAACCA ATGAAAAAGA AAAAAGTTGG CCGTAAACCA AAGACCCAGC    720
AATCACCAAT TTCCAATGGG TCTCCTGAGT TAGGTATAAA GAAGAAACCA AGAGAAGGAA    780
AAGGAAACAC AACCTATTTG TGGGAGTTTC TTTTAGATCT ACTTCAAGAT AAAAATACTT    840
GTCCCAGGTA TATTAAATGG ACTCAGAGAG AAAAAGGCAT ATTCAAGCTG GTGGATTCAA    900
AGGCTGTCTC TAAGCTTTGG GGAAAGCATA AGAACAAACC AGACATGAAC TATGAAACCA    960
TGGGACGAGC TTTGAGATAC TACTACCAAA GGGGAATTCT TGCAAAGGTT GAAGGACAGA   1020
GGCTTGTATA TCAGTTCAAG GATATGCCGA AAAACATAGT GGTCATAGAT GATGACAAAA   1080
GTGAAACCTG TAATGAAGAT TTAGCAGGAA CTACTGATGA AAAATCATTA GAACGAGTGT   1140
CACTGTCTGC AGAAAGTCTC CTGAAAGCAG CATCCTCTGT TCGCAGTGGA AAAAATTCAT   1200
CCCCTATAAA CTGCTCCAGA GCAGAGAAGG GTGTAGCTAG AGTTGTGAAT ATCACTTCCC   1260
CTGGGCACGA TGCTTCATCC AGGTCTCCTA CTACCACTGC ATCTGTGTCA GCAACAGCAG   1320
CTCCAAGGAC AGTTCGTGTG GCAATGCAGG TACCTGTTGT AATGACATCA TTGGGTCAGA   1380
AAATTTCAAC TGTGGCAGTT CAGTCAGTTA ATGCAGGTGC ACCATTAATA ACCAGCACTA   1440
GTCCAACAAC AGCGACCTCT CCAAAGGTAG TCATTCAGAC AATCCCTACT GTGATGCCAG   1500
CTTCTACTGA AAATGGAGAC AAAATCACCA TGCAGCCTGC CAAAATTATT ACCATCCCAG   1560
CTACACAGCT TGCACAGTGT CAACTGCAGA CAAAGTCAAA TCTGACTGGA TCAGGAAGCA   1620
TTAACATTGT TGGAACCCCA TTGGCTGTGA GAGCACTTAC CCCTGTTTCA ATAGCCCATG   1680
GTACACCTGT AATGAGACTA TCAATGCCTA CTCAGCAGGC ATCTGGCCAG ACTCCTCCTC   1740
GAGTTATCAG TGCAGTCATA AAGGGGGCAG AGGTTAAATC GGAAGCAGTG GCAAAAAAGC   1800
AAGAACATGA TGTGAAAACT TGGAGCTAG TAGAAGAAAA ACCAGCAGAT GGAAATAAGA   1860
CAGTGACCCA CGTAGTGGTT GTCAGTGCGC CTTCAGCTAT TGCCCTTCCT GTAACTATGA   1920
AAACAGAAGG ACTAGTGACA TGTGAGAAAT AAAATAGCAG CTCCACCATG GACTTCAGGC   1980
TGTTAGTGGC AGTACTGACA TAAACATTTG CAAGGGAAGT CATCAAGAAA AGTCCAAAGA   2040
AGACTTTAAA ACATTTTTAA TGCATATACA AAAACAATCA GACTTACTGG AAATAAATTA   2100
CCTATCCCAT GTTTCAGTGG GAAATGAACT ACATATTGAG ATGCTGACAG AAAACTGCCT   2160
CTTACAGTAG GAAACAACTG AACCCATCAA TAAGAAAAAG GATCGAAAGG GACCAAGCAG   2220
CTCACTACGA TATCAAGTTA CACTAAGACT TGGAACACTA ACATTCTGTA AGAGGTTATA   2280
TAGTTTTTCA GTGGGAGGGG TTGGGATGGG TAATCTCATT GTTACATATA GCAATTTTTG   2340
ATGCATTTTA TATGCATACC AGCAATTATT ACTGTGTTCG CACAGTTCTC ACTTAACTGG   2400
TGCTATGTGA AGACTCTGCT AATATAGGTA TTTTAGAATG TGAATTGAAG AATGGATCCC   2460
AAAAACTTCA GAAAGAGGAT AGCAAAAAAA GATCTAGTGC GATTTTATAT ATATATATAT   2520
ATATATATAC ATACATATAT ATATATCATA TAGCTTAAGC TGATTTAAAA CAAAGGCCTT   2580
AGACTAATTT TCGATTTTCT TTCTTGAAAT AAGCTAATGG CTTGTTTGTG TAAAGCTTTT   2640
TTATTAAAAG AAAAATTTTA AAAATCTTGT ACCTAGCACA GTATTGTTAT AGAATATACA   2700
TGTAACATTT TATATGGTAG TTTAAGTCTG TCAGTTTCTT AATTGTGGAC AAATTAACAG   2760
TTGGCTCTGG CCTTTTGCTG TAACATGCCT GTGTCACTCA CTTAGCCTTG GCATTTGTGC   2820
AGACATACCA TTTTCAGTTC TGCTGTCACT TGGAAGTTCA GGCTCAGCAT GAATTTTGG   2880
CAGGTAGCTC TAATACCTGG AGTTTTCTTT GTTTTTTTT CTTTTTTTA GTTGAAGTTT   2940
ATGAGGGAAA TACCAGTGTT CAGTTTTGAA CTATAATAGT TTGTATATTC AACATTTGAA   3000
GTATATTCTA TTTTGTTGTA CTCTTGTTTC AAAGTGTATT CAAGTAGGTT TTCTGAAATA   3060
```

```
TAGAAATGAA ATTTATCTTC TGTTTTGGTC TCTGGTGATA TTTTAAACAA TATTTAAAAG    3120

TCAGTATAGA AGTGTTTTAG TTAGGAAGTG ATAAACATC  TCTCTTCTCC TTCCCAACTA    3180

CTGCATGAAG AAATTCTACT TCCATTATAT TAATATTTGG GCAAAAAAAA AAAAAAAAA     3240
```

( 2 ) INFORMATION FOR SEQ ID NO:4:

( i ) SEQUENCE CHARACTERISTICS:
        ( A ) LENGTH: 581 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Ser Ala Val Val Asp Ser Gly Gly Thr Ile Leu Glu Leu Ser
 1               5                  10                 15

Ser Asn Gly Val Glu Asn Gln Glu Glu Ser Asp Lys Val Ser Glu Tyr
            20                  25                  30

Pro Ala Val Ile Val Glu Pro Val Pro Ser Ala Arg Leu Glu Gln Gly
        35                  40                  45

Tyr Ala Ala Gln Val Leu Gly Tyr Asp Asp Glu Thr Tyr Leu Met Gln
     50                  55                  60

Asp Val Ala Glu Glu Gln Glu Val Glu Thr Glu Asn Ala Glu Thr Val
 65                  70                  75                  80

Glu Ala Ser Val His Ser Ser Asn Ala His Cys Thr Asp Lys Thr Ile
                 85                  90                  95

Glu Ala Ala Glu Ala Leu Leu His Met Glu Ser Pro Thr Cys Leu Arg
            100                 105                 110

Asp Ser Arg Ser Pro Glu Phe Ile His Ala Ala Met Arg Pro Asp Val
        115                 120                 125

Ile Thr Glu Thr Val Val Glu Val Ser Thr Glu Glu Ser Glu Pro Met
    130                 135                 140

Asp Thr Ser Pro Ile Pro Thr Ser Pro Asp Ser His Glu Pro Met Lys
145                 150                 155                 160

Lys Lys Lys Val Gly Arg Lys Pro Lys Thr Gln Gln Ser Pro Ile Ser
                165                 170                 175

Asn Gly Ser Pro Glu Leu Gly Ile Lys Lys Pro Arg Glu Gly Lys
            180                 185                 190

Gly Asn Thr Thr Tyr Leu Trp Glu Phe Leu Leu Asp Leu Leu Gln Asp
        195                 200                 205

Lys Asn Thr Cys Pro Arg Tyr Ile Lys Trp Thr Gln Arg Glu Lys Gly
    210                 215                 220

Ile Phe Lys Leu Val Asp Ser Lys Ala Val Ser Lys Leu Trp Gly Lys
225                 230                 235                 240

His Lys Asn Lys Pro Asp Met Asn Tyr Glu Thr Met Gly Arg Ala Leu
                245                 250                 255

Arg Tyr Tyr Tyr Gln Arg Gly Ile Leu Ala Lys Val Glu Gly Gln Arg
            260                 265                 270

Leu Val Tyr Gln Phe Lys Asp Met Pro Lys Asn Ile Val Ile Asp
        275                 280                 285

Asp Asp Lys Ser Glu Thr Cys Asn Glu Asp Leu Ala Gly Thr Thr Asp
    290                 295                 300

Glu Lys Ser Leu Glu Arg Val Ser Leu Ser Ala Glu Ser Leu Leu Lys
305                 310                 315                 320

Ala Ala Ser Ser Val Arg Ser Gly Lys Asn Ser Ser Pro Ile Asn Cys
```

|           |           |           |           |           | 325       |           |           |           | 330       |           |           |           | 335       |           |
|-----------|-----------|-----------|-----------|-----------|-----------|-----------|-----------|-----------|-----------|-----------|-----------|-----------|-----------|-----------|
| Ser | Arg | Ala | Glu 340 | Lys | Gly | Val | Ala | Arg 345 | Val | Val | Asn | Ile | Thr 350 | Ser | Pro |

Gly His Asp Ala Ser Ser Arg Ser Pro Thr Thr Thr Ala Ser Val Ser
      355                        360                365

Ala Thr Ala Ala Pro Arg Thr Val Arg Val Ala Met Gln Val Pro Val
      370                  375                380

Val Met Thr Ser Leu Gly Gln Lys Ile Ser Thr Val Ala Val Gln Ser
385               390                    395                    400

Val Asn Ala Gly Ala Pro Leu Ile Thr Ser Thr Ser Pro Thr Thr Ala
              405                  410                    415

Thr Ser Pro Lys Val Val Ile Gln Thr Ile Pro Thr Val Met Pro Ala
          420              425                    430

Ser Thr Glu Asn Gly Asp Lys Ile Thr Met Gln Pro Ala Lys Ile Ile
        435              440              445

Thr Ile Pro Ala Thr Gln Leu Ala Gln Cys Gln Leu Gln Thr Lys Ser
    450              455              460

Asn Leu Thr Gly Ser Gly Ser Ile Asn Ile Val Gly Thr Pro Leu Ala
465              470              475                        480

Val Arg Ala Leu Thr Pro Val Ser Ile Ala His Gly Thr Pro Val Met
              485                  490                    495

Arg Leu Ser Met Pro Thr Gln Gln Ala Ser Gly Gln Thr Pro Pro Arg
            500                  505              510

Val Ile Ser Ala Val Ile Lys Gly Ala Glu Val Lys Ser Glu Ala Val
        515              520              525

Ala Lys Lys Gln Glu His Asp Val Lys Thr Leu Glu Leu Val Glu Glu
    530                  535              540

Lys Pro Ala Asp Gly Asn Lys Thr Val Thr His Val Val Val Val Ser
545                  550              555                    560

Ala Pro Ser Ala Ile Ala Leu Pro Val Thr Met Lys Thr Glu Gly Leu
              565                  570              575

Val Thr Cys Glu Lys
            580

(2) INFORMATION FOR SEQ ID NO:5:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

CTGGTTCGGC CCACCTCTGA AGGTTCCAGA ATCGATAG         38

(2) INFORMATION FOR SEQ ID NO:6:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:6:

AGAGACAGCC TTTGAATCCA CCAGC         25

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CTCAGGAGAC CCATTGGAAA TTGGTG  26

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CGGATGAGCA GATCCAGCTG GTTCG  25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CCTGCTCTAA TCTGGCACTT GGAAC  25